United States Patent [19]
Gohla et al.

[11] Patent Number: 5,861,440
[45] Date of Patent: Jan. 19, 1999

[54] COSMETIC AND MEDICINAL TOPICAL PREPARATIONS

[75] Inventors: Sven Gohla, Hamburg; Friedrich Heinze, Frankfurt am Main; Jens Nielsen, Norderstedt; Carl Thamssen, Hamburg, all of Germany

[73] Assignee: Beiersdorf Aktiengesellschaft, Hamburg, Germany

[21] Appl. No.: 537,706

[22] PCT Filed: Apr. 13, 1994

[86] PCT No.: PCT/EP94/01145

§ 371 Date: Jan. 3, 1996

§ 102(e) Date: Jan. 3, 1996

[87] PCT Pub. No.: WO94/23688

PCT Pub. Date: Oct. 27, 1994

[30] Foreign Application Priority Data

Apr. 19, 1993 [DE] Germany ............ 43 12 656.1

[51] Int. Cl.⁶ .................................................. A61K 31/045
[52] U.S. Cl. .................. 514/738; 424/400; 424/401; 424/489; 424/490; 514/844; 514/847; 514/848; 514/873

[58] Field of Search .................. 424/59, 65, 400, 424/401, 489, 490; 514/738, 844, 847, 848, 873

[56] References Cited

U.S. PATENT DOCUMENTS 4,427,010  1/1984  Marx .................................. 607/114

FOREIGN PATENT DOCUMENTS 0259982  3/1988  European Pat. Off. .
0303461  8/1988  European Pat. Off. .

*Primary Examiner*—Shelley A. Dodson
*Attorney, Agent, or Firm*—Sprung Kramer Schaefer & Briscoe

[57] ABSTRACT

The use of substances that are generally recognized as safe for cosmetic or pharmaceutical applications and that have positive solution enthalpy, in particular sugar alcohols of general formula (I) where N=3, 4 and 5, preferably xylitol, in cosmetic or medicinal topical preparations is characterized in that the substances or substances in the preparations are present in a largely water-free medium and/or are shielded from an aqueous medium by a material barrier.

11 Claims, No Drawings

COSMETIC AND MEDICINAL TOPICAL PREPARATIONS

The present invention relates to cosmetic and medicinal topical care formulations, in particular those which, when applied to the skin or mucous membranes, have a moisturizing and cooling effect.

Such compositions are known per se. Described in the literature as cooling agents are, for example, ionic compounds, in particular ammonium salts. Isopropanol gels with an addition of camphor and menthol are also widely used as cooling formulations.

Essential oils, mostly camphor and menthol, but also their derivatives, for example menthyl lactate or menthyl 3-hydroxybutyrate, are generally frequently incorporated into cooling compositions.

Menthol and camphor and their derivatives, but also other essential oils, reduce the stimulus threshold of the neuronal thermoreceptors, causing a cold sensation. However, frequently they favour the blood flow at the same time and this, on the contrary, causes a warm sensation.

In any case, the use of these substances causes problems, in particular on irritated skin. Moreover, the water solubility of many of these compounds is poor. As a consequence, their use is limited to a few cosmetics and products for dermal use.

It was therefore an object of the present invention to provide cosmetic and medicinal care formulations which do not have the shortcomings of the prior art, in particular those which, when applied to the skin or mucous membranes, have a moisturizing and/or cooling effect.

This object is achieved according to the invention by using cosmetically or pharmacologically acceptable substances having a positive solution enthalpy in cosmetic or medicinal topical formulations, characterized in that the substance, or the substances, are present in the formulations in an essentially anhydrous medium and/or are protected from an aqueous medium by means of a physical barrier.

As a particularly advantageous embodiment of the present invention, the object is achieved by cosmetic and dermatological compositions containing one or more sugar alcohols of the general formula

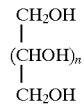

where n=3, 4 and 5
and
where the sugar alcohol, or the sugar alcohols, are present in the formulations in an essentially anhydrous medium and/or are protected from an aqueous medium by means of a physical barrier.

It is known that some sugar alcohols have a positive solution enthalpy when dissolved in water under standard conditions, i.e. the temperature of the solution drops during the dissolution process. From amongst the sugar alcohols, xylitol has the highest positive solution enthalpy. Xylitol is the preferred sugar alcohol used according to the invention.

Xylitol, as represented by the Fischer projection, has the structural formula

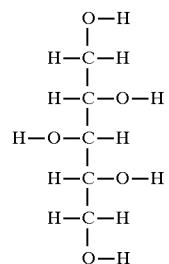

It has the meso configuration and is therefore not optically active.

Xylitol (xylo-pentanepentol) can be obtained industrially by hydrogenating xylose and is employed, for example, as the sugar substitute for diabetics. Occasionally, it is used as a humectant in cosmetic formulations.

However, it was unknown to utilize the positive solution enthalpy of cosmetically or pharmacologically acceptable substances in general or of the sugar alcohols according to the invention in particular for use in cosmetic or medicinal topical formulations which have a cooling effect.

Other substances which are active according to the invention are uronic acids of the general formula

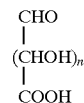

where n=3, 4 and 5
(or their cyclic forms) and their salts as long as these uronic acids, or uronic acid salts, are distinguished by a positive solution enthalpy and by cosmetic or pharmacological acceptability.

An advantageous uronic acid salt according to the invention is sodium mannuronate, which is distinguished by the following structure:

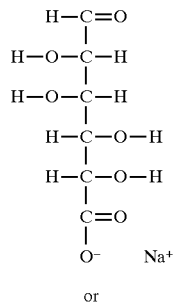

or

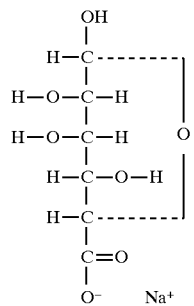

It was particularly surprising that the cooling effect of xylitol can be increased even more according to the invention in combination with substances selected from the group comprising mannitol, sorbitol, propylene glycol, glycerol, urea, 2-pyrrolidone-5-carboxylic acid and its sodium salt, and also sodium mannuronate. Relative to the cooling effect of the individual substances, the increase in the cooling effect is superadditive, which means that a synergism is present.

Moreover, the mixtures of xylitol and this group of substances are distinguished, surprisingly, by particularly favourable skincare properties. In particular, the skin-moisturizing capacity of xylitol is markedly increased.

Within the scope of the present invention, it is possible and, if appropriate, advantageous to employ such mixtures even in cosmetic or medicinal topical formulations which contain large amounts of water. If appropriate, the cooling effect is somewhat less important in this context.

Particularly advantageous mixtures are mixtures of xylitol and at least one of the substances selected from the group comprising mannitol, sorbitol, glycerol, propylene glycol, urea, 2-pyrrolidone-5-carboxylic acid, sodium 2-pyrrolidone-5-carboxylate, sodium mannuronate, $NH_4Cl$ and tartaric acid and/or its salts.

The xylitol content in such mixtures can advantageously be 0.5–99.5 % by weight based on the total weight of these compositions.

Other advantageous compositions are those containing
0.5–10.0 parts of xylitol
0.0–5.0 parts of mannitol
0.0–5.0 parts of sorbitol
0.0–5.0 parts of glycerol
0.0–5.0 parts of propylene glycol
0.0–5.0 parts of urea
0.0–5.0 parts of 2-pyrrolidone-5-carboxylic acid
0.0–5.0 parts of sodium 2-pyrrolidone-5-carboxylate
0.0–5.0 parts of sodium mannuronate
0.0–5.0 parts of $NH_4Cl$
0.0–5.0 parts of one or more tartrates,
based on the total composition of the formulation, with the proviso that at least one of the non-xylitol components is present at a concentration of at least 0.1% by weight.

These combinations preferably contain
1.0–8.0 parts of xylitol
0.0–3.0 parts of mannitol
0.0–3.0 parts of sorbitol
0.0–3.0 parts of glycerol
0.0–3.0 parts of propylene glycol
0.0–3.0 parts of urea
0.0–3.0 parts of 2-pyrrolidone-5-carboxylic acid
0.0–3.0 parts of sodium 2-pyrrolidone-5-carboxylate
0.0–3.0 parts of sodium mannuronate
0.0–3.0 parts of NH4Cl
0.0–3.0 parts of one or more tartrates,
based on the total composition of the formulation, with the proviso that at least one of the non-xylitol components is present at a concentration of at least 0.5% by weight.

These combinations very particularly preferably contain
2.0–5.0 parts of xylitol
0.0–2.5 parts of mannitol
0.0–2.5 parts of sorbitol
0.0–2.5 parts of glycerol
0.0–2.5 parts of propylene glycol
0.0–2.5 parts of urea
0.0–2.5 parts of 2-pyrrolidone-5-carboxylic acid
0.0–2.5 parts of sodium 2-pyrrolidone-5-carboxylate
0.0–2.5 parts of sodium mannuronate
0.0–2.5 parts of $NH_4Cl$
0.0–2.5 parts of one or more tartrates,
based on the total composition of the formulation, with the proviso that at least one of the non-xylitol components is present at a concentration of at least 1.0% by weight.

The physical barrier according to the invention can consist, for example, in employing the substance, or the substances, which have a positive solution enthalpy in microencapsulated form.

If it is desired to protect the substance, or the substances, in the formulations from an aqueous medium by means of microencapsulation, then the processes conventionally used for this method can be employed. A typical process is to dissolve the shell material in a solvent—in the form of a colloidal or true solution—and to disperse the core material, i.e. what is to become the content of the microcapsules, in the resulting solution in the form of solids or microdroplets.

This dispersion is divided into microdroplets and then sprayed into a heated medium, for example hot air. During this process, the solvent evaporates. The shell material reprecipitates in the form of solids and forms a shell around the core material. This already gives crude microcapsules which can then be subjected to the customary processing steps and incorporated into the final formulations. This process utilizes the known phenomenon of coacervation.

Another possibility consists in creating the shell of the microcapsules by means of interface polymerization of the shell material. This means that not the final shell material as such is employed, but rather precursors, for example monomers, which concentrate on the core material, where they polymerize to give the final shell film.

Fat-coating processes are also advantageous embodiments of the process according to the invention.

The materials used for microencapsulation can advantageously be selected from amongst the conventional hydrophilic or hydrophobic substances or mixtures thereof. Solids, in particular natural polymers, for example, starch and other polysaccharides, are preferred. However, synthetic polymers can also be used advantageously.

Examples of shell materials are fats and/or waxes, preferably those having a solidification temperature of approximately 35°–80° C. Mixtures of cetyl palmitate and cetyl alcohol are particularly advantageous.

The following are also advantageous: polysaccharides and their derivatives of natural or partially synthetic origin, in particular cellulose derivatives, which are, in particular, also to be understood as including chitin derivatives; furthermore polymers of α- and/or β-hydroxycarboxylic acids, in particular polymers of glycolic acid (polyglycolides), lactic acid (polylactides), α-hydroxybutyric acid (polyhydroxybutyrate), α-hydroxyvaleric acid (polyhydroxyvalerate) and/or their copolymers, or mixtures of such polymers and/or copolymers.

Independently of the preparation process used for the microcapsules according to the invention, it is preferred in each case to carry out the process at a temperature which does not exceed the melting point of the core material. In the case of pure xylitol, this means that the process should not be carried out at a temperature of above 90° C.

As is known to the expert, the microcapsules can be opened in various ways. For example, they can be disrupted by mechanical force or else opened by chemical, for example enzymatic, processes, releasing the active substance, or the active substances, from the core of the capsule.

It is furthermore advantageous for the solubility of the core material in the solvent to be as low as possible.

The cosmetic and/or dermatological formulations according to the invention can be composed as usual and can be used for treating the skin and/or the hair in the sense of a dermatological treatment or a treatment in the sense of cosmetic care. Alternatively, they can also be employed in make-up products in decorative cosmetics. They contain preferably 0.01% by weight to 30% by weight, but, in particular, 0.1% by weight to 10% by weight, of cosmetically or pharmacologically acceptable substances which have a positive solution enthalpy, in particular sugar alcohols, particularly preferably xylitol, as long as it is guaranteed that the substance, or the substances, are present in the formulations in an essentially anhydrous medium and/or are protected from an aqueous medium by means of a physical barrier.

For use, a sufficient amount of the formulations according to the invention are applied to the skin in a manner which is customary for cosmetics and dermatics.

The formulations according to the invention can exist in a variety of forms. For example, they can be a solution, an emulsion of the water-in-oil type (W/o) or the oil-in-water type (O/W), or multiple emulsions, for example of the water-in-oil-in-water type (W/o/W), a gel, a hydrodispersion, a solid stick or else an aerosol.

The cosmetic formulations according to the invention can contain cosmetic auxiliaries as they are conventionally used in such formulations, for example preservatives, bactericides, perfumes, foam inhibitors, colourants, pigments having a colouring action, thickeners, surface-active substances, emulsifiers, plasticizers, moisturizers and/or humectants, fats, oils, waxes or other conventional components of a cosmetic product, such as alcohols, polyols, polymers, foam stabilizers, electrolytes, organic solvents or silicone derivatives.

If the cosmetic or dermatological formulation is a solution or emulsion, the following can be used as solvents:

water or aqueous solutions;

oils, such as triglycerides of capric or caprylic acid, but preferably castor oil;

fats, waxes and other natural and synthetic fatty substances, preferably esters of fatty acids with alcohols having a low C number, for example with isopropanol, propylene glycol or glycerol, or esters of fatty alcohols with alkanoic acids having a low C number, or with fatty acids;

alcohols, diols or polyols having a low C number, and their ethers, preferably ethanol, isopropanol, propylene glycol, glycerol, ethylene glycol, ethylene glycol monoethyl ether, ethylene glycol monobutyl ether, propylene glycol monomethyl ether, propylene glycol monoethyl ether, propylene glycol monobutyl ether, diethylene glycol monomethyl ether or diethylene glycol monoethyl ether, and analogous products.

In particular, mixtures of the abovementioned solvents are used. In the case of alcoholic solvents, water can be a further component.

Gels according to the invention conventionally contain alcohols having a low C number, for example ethanol, isopropanol, 1,2-propanediol, glycerol and water, or an oil which has been mentioned above, in the presence of a thickener which is, in the case of oily/alcoholic gels, preferably silicon dioxide or an aluminium silicate and, in the case of aqueous/alcoholic or alcoholic gels, preferably a polyacrylate. Furthermore, such gels can contain gum arabic, xanthane gum, sodium alginate, cellulose derivatives, preferably methylcellulose, hydroxymethylcellulose, hydroxyethylcellulose, hydroxypropylcellulose, hydroxypropylmethylcellulose, or inorganic thickeners, for example aluminium silicates, such as, for example, bentonites, or a mixture of polyethylene glycol and polyethylene glycol stearate or polyethylene glycol distearate. The gel contains the thickener, for example, in an amount of between 0.1 and 30% by weight, preferably between 0.5 and 15% by weight.

Solid sticks according to the invention contain, for example, natural or synthetic waxes, fatty alcohols, metal soaps or fatty acid esters.

Propellants which are suitable for cosmetic or dermatological formulations according to the invention which can be sprayed from aerosol containers are the customary, known, volatile, liquefied propellants, for example hydrocarbons (propane, butane, isobutane), which can be employed by themselves or in the form of a mixture with each other. It is also advantageous to use compressed air.

It is, of course, known to a person skilled in the art that there are propellants which are non-toxic as such and which could be basically suitable for the present invention, but which should nevertheless not be used since their effect on the environment is not acceptable, or for other related reasons, in particular fluorohydrocarbons and fluorochlorohydrocarbons (FCHC).

The formulations according to the invention can advantageously be in the form of deodorizing cosmetics. In this case, they contain one or more substances from amongst the group of substances which are conventionally used as substances with a deodorizing or antiperspirant action. Aluminium chloride hydrate, but also mixtures as they are described, for example, in DE-OS 37 40 186, are advantageous.

The formulations according to the invention can also preferably contain substances which absorb UV radiation in the UVB range, the total amount of the filter substances being, for example, 0.1% by weight to 30% by weight, preferably 0.5 to 10% by weight, in particular 1 to 6% by weight, relative to the total weight of the formulation, in order to provide cosmetic formulations which protect the skin against the entire range of ultraviolet radiation. They can also be used as suntan products.

Emulsions according to the invention, for example in the form of a suntan cream, a suntan lotion or a suntan milk, are advantageous and contain, for example, the abovementioned fats, oils, waxes and other fatty substances, as well as water and an emulsifier as it is conventionally used for such a type of product.

The UVB filters can be oil-soluble or water-soluble. Advantageous oil-soluble UVB filters are, for example:

3-benzylidenecamphor derivatives, preferably 3-(4-methylbenzylidene)camphor, 3-benzylidene-camphor;

4-aminobenzoic acid derivatives, preferably 2-ethylhexyl 4-(dimethylamino)benzoate, amyl 4-(dimethylamino) benzoate;

cinnamic esters, preferably 2-ethylhexyl 4-methoxycinnamate, isopentyl 4-methoxycinnamate;

salicylic esters, preferably 2-ethylhexyl salicylate, 4-isopropylbenzyl salicylate, homomenthyl salicylate;

benzophenone derivatives, preferably 2-hydroxy-4-methoxybenzophenone, 2-hydroxy-4-methoxy-4'-methylbenzophenone, 2,2'-dihydroxy-4-methoxybenzophenone;

benzylmalonic esters, preferably di(2-ethylhexyl) 4-methoxybenzylmalonate;

2,4,6-trianilino(p-carbo-2'-ethyl-1'-hexyloxy)-1,3,5-triazine.

Advantageous water-soluble UVB filters are, for example:

salts of 2-phenylbenzimidazole-5-sulphonic acid, such as sodium, potassium or triethanolammonium and the sulphonic acid itself;

sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)-benzenesulphonic acid, 2-methyl-S-(2-oxo-3-bornylidenemethyl)sulphonic acid and its salts;

Naturally, the list of the abovementioned UVB filters is not by way of limitation.

Examples of UVA filters which can be used advantageously according to the invention are dibenzoylmethane derivatives, in particular 1-(4'-tert-butyl-phenyl)-3-(4'-methoxyphenyl)propane-1,3-dione and 1-phenyl-3-(4'-isopropylphenyl)propane-1,3-dione. The amounts used for the UVB combination can be in employed.

Naturally, the list of the abovementioned UVA filters is equally not by way of limitation.

The formulations according to the invention can also contain inorganic pigments which are conventionally used in cosmetics for protecting the skin against UV rays. These are oxides of titanium, zinc, iron, zirconium, silicon, manganese, aluminium, cerium and mixtures of these, and modifications in which the oxides are the active agents. They are particularly preferably titanium-dioxide-based pigments.

Cosmetic and dermatological formulations which are also advantageous are those in the form of a suntan product, a before-sun or after-sun product. These advantageously additionally contain at least one UVA filter and/or at least one UVB filter and/or at least one inorganic pigment.

The examples which follow are intended to illustrate the present invention in greater detail, without it being intended to restrict the invention to these examples.

The examples 1–10 show advantageous combinations according to the invention.

These combinations or the individual substances according to the invention, advantageously xylitol itself, can be microencapsulated, as shown in Examples 11–13, and incorporated into cosmetic or medicinal topical formulations, as shown in Examples 14–29.

| Example | 1 | 2 | 3 | 4 | 5 |
|---|---|---|---|---|---|
| Xylitol | 5.00 | 10.00 | 3.00 | 10.00 | 7.50 |
| Mannitol | 1.00 | 1.00 | — | 2.00 | 1.00 |
| Sorbitol | 0.30 | — | 1.00 | — | 1.00 |
| Glycerol | 2.00 | — | — | 2.00 | 2.00 |
| PG | 1.00 | — | — | 1.00 | — |
| Urea | 2.00 | 1.00 | — | 1.00 | 3.00 |
| PCA | 1.00 | — | 1.00 | — | — |
| NaPCA | 0.50 | — | — | — | — |
| NaMu | 0.30 | — | — | — | — |
| NH$_4$Cl | 2.00 | 3.00 | 3.00 | 1.50 | 1.00 |
| NaTa | 1.50 | 2.00 | 1.00 | 2.50 | 3.00 |

| Example | 6 | 7 | 8 | 9 | 10 |
|---|---|---|---|---|---|
| Xylitol | 16.50 | 4.50 | 6.00 | 8.00 | 7.00 |
| Mannitol | 3.50 | 2.30 | 1.00 | — | 2.00 |
| Sorbitol | — | 1.00 | 1.00 | — | — |
| Glycerol | 2.00 | 2.00 | — | 1.00 | 3.00 |
| PG | — | 2.00 | — | — | — |
| Urea | 3.00 | — | 1.00 | 1.00 | 1.00 |
| PCA | — | — | 1.00 | — | — |
| NaPCA | — | 1.00 | — | — | — |
| NaMu | 1.00 | — | — | — | — |
| NH$_4$Cl | 1.50 | 3.00 | 1.00 | 1.00 | 5.00 |
| NaTa | 1.50 | 2.00 | 2.50 | 3.00 | 1.00 |

PG = propylene glycol
PCA = 2-pyrrolidone-5-carboxylic acid
NaPCA = sodium 2-pyrrolidone-5-carboxylate
NaMu = sodium mannuronate
NaTa = sodium tartrate (=C$_4$H$_4$Na$_2$O$_6$ * 2 H$_2$O)

The numerical values are parts by weight.

Example 11

Xylitol is introduced in micronized form. A mixture of polylactide and methylcellulose in a ratio of 1:10, which is in the form of a solution in chloroform and which has been heated at a temperature of 60° C., is applied to the xylitol particles via a nozzle using the fluidized-bed method.

This gives a high yield of microcapsules which contain xylitol in solid form.

Example 12

Xylitol in micronized form is introduced into a kneader mixer suitable for mixing powders. A triglyceride mixture (Witepsol®, high-melting-point variants, Dynamit Nobel) is combined, at 40° C., with the micronized xylitol. The resulting mixture is cooled to room temperature with continuous vigorous agitation.

This gives a high yield of microcapsules which contain xylitol in solid form.

Example 13

A mixture as described in Example 1 is introduced in micronized form. A mixture of polylactide and methylcellulose in a ratio of 1:10, which is in the form of a solution in chloroform and which has been heated at a temperature of 60° C., is applied to the solid particles using the fluidized-bed method.

This gives a high yield of microcapsules which contain a mixture as described in Example 1 in solid form.

Example 14

| Regenerating night cream | |
|---|---|
| | % by weight |
| Glycerol sorbitan oleostearate | 5.00 |
| Ceresin | 3.00 |
| Miglyol 812 | 3.60 |
| Capryl/caproyl/isostearyl/adipic triglyceride | 1.00 |
| Isoectyl stearate | 6.00 |
| PEG-22/dodecyl glycol copolymer | 1.50 |
| Olive oil | 2.00 |
| Microcapsules as described in Example 11 | 5.00 |
| MgSO$_4$ | 0.60 |
| Polyhexamethylene biguanide | 0.20 |
| Tocopheryl acetate | 0.50 |
| Cyclomethicone | 2.00 |
| Kollan PM | 0.50 |
| Fibronectin | 0.50 |
| Perfume, colourants preservatives | q.s. |
| H$_2$O | to 100.00 |

Example 15

Intensive day cream

| | % by weight |
|---|---|
| Glycerol sorbitan oleostearate | 5.00 |
| Ceresin | 3.00 |
| Miglyol 812 | 4.10 |
| Capryl/caproyl/isostearyl/adipic triglyceride | 1.00 |
| Isoectyl stearate | 6.00 |
| PEG-45/dodecyl glycol copolymer | 1.50 |
| Octyl methoxycinnamate | 1.00 |
| Butylmethoxydibenzoylmethane | 0.50 |
| Microcapsules as described in Example 12 | 6.20 |
| $MgSO_4$ | 0.60 |
| EDTA solution | 0.50 |
| Isohexadecane | 2.00 |
| Tocopheryl acetate | 0.50 |
| Kollan PM | 0.50 |
| Fibronectin | 0.50 |
| Perfume, colourants, preservatives | q.s. |
| $H_2O$ | to 100.00 |

Example 16

Body lotion

| | % by weight |
|---|---|
| Arlatone 985 | 4.00 |
| Brij 78 | 2.00 |
| Miglyol 812 | 5.00 |
| Liquid paraffin DAB 9 | 5.00 |
| Microcapsules as described in Example 13 | 5.00 |
| Perfume, colourants, preservatives | q.s. |
| $H_2O$ | to 100.00 |

Example 17

Cleansing emulsion

| | % by weight |
|---|---|
| Cutina MD | 4.00 |
| Lanette O | 2.00 |
| Emulgin B1 | 1.50 |
| Rilanit GMO | 1.50 |
| Cetiol SN | 1.00 |
| Soft liquid paraffin DAB 8 | 10.00 |
| Microcapsules as described in Example 11 | 25.00 |
| Propylene glycol | 5.00 |
| Liquid paraffin DAB 9 | 0.50 |
| Perfume, colourants, preservatives | q.s. |
| $H_2O$ | to 100.00 |

Example 18

Lipo-cream

| | % by weight |
|---|---|
| Beeswax and PEG-8 | 8.00 |
| Cetyl alcohol | 1.00 |
| $C_{12}$–$C_{15}$-alcohol benzoate | 7.00 |
| Octyldodecyl myristate | 5.00 |
| Cyclomethicone | 2.00 |
| Tocopheryl acetate | 1.10 |
| NaOH | 0.14 |
| Carbomer 934 | 0.35 |

-continued

Lipo-cream

| | % by weight |
|---|---|
| Microcapsules as described in Example 12 | 5.00 |
| Alcohol SD 39-C | 1.00 |
| Perfume, colourants, preservatives | q.s. |
| $H_2O$ | to 100.00 |

Example 19

W/O emulsion, liquid

| | % by weight |
|---|---|
| Elfacos E 200 | 2,00 |
| Elfacos ST 9 | 5.00 |
| Elfacos C 26 | 5.00 |
| Isopropyl stearate | 20.00 |
| Microcapsules as described in Example 13 | 5.00 |
| Perfume, colourants, preservatives | q.s. |
| $H_2O$ | to 100.00 |

Example 20

After-sun lotion

| | % by weight |
|---|---|
| Solulan PB 20 | 10.00 |
| Solulan PB 2 | 5.00 |
| Isopropyl palmitate | 10.00 |
| Carbopol 934 P | 0.75 |
| NaOH | 2.25 |
| Ethomeen C25 (10%) | 3.75 |
| Microcapsules as described in Example 11 | 5.00 |
| Perfume, colourants, preservatives | q.s. |
| $H_2O$ | to 100.00 |

Example 21

Body splash

| | % by weight |
|---|---|
| Ethanol | 40.00 |
| Carbopol 940 | 0.40 |
| Diisopropanolamine | 0.40 |
| Uvinul D50 | 0.05 |
| Polyethyleneglycol-2000 monooleate | 5.00 |
| Microcapsules as described in Example 12 | 10.00 |
| Perfume, colourants, preservatives | q.s. |
| $H_2O$ | to 100.00 |

Example 22

Face tonic

| | % by weight |
|---|---|
| Chlorhexidine gluconate | 0.10 |
| Ethanol | 5.00 |
| Elastin | 3.00 |
| Cremophor RH 40 | 0.20 |
| Microcapsules as described in Example 13 | 4.00 |

11
-continued

Face tonic

| | % by weight |
|---|---|
| Perfume, colourants, preservatives | q.s. |
| H₂O | to 100.00 |

Example 23

Aftershave

| | % by weight |
|---|---|
| Tagat S | 2.20 |
| Tegin M | 1.60 |
| Isopropyl myristate | 8.60 |
| Liquid paraffin DAB 9 | 8.20 |
| Microcapsules as described in Example 11 | 5.00 |
| Citric acid | 0.20 |
| KA1 (SO₄)₂ * 12 H₂O | 0.10 |
| Lactic acid | 2.00 |
| Bisabolol | 0.07 |
| Perfume, colourants, preservatives | q.s. |
| H₂O | to 100.00 |

Example 24

Skin gel

| | % by weight |
|---|---|
| Emulgin B3 | 13.00 |
| Cetiol HE | 20.00 |
| Eutanol G | 5.00 |
| Microcapsules as described in Example 12 | 5.00 |
| Perfume, colourants, preservatives | q.s. |
| H₂O | to 100.00 |

Example 25

Deordorant spray

| | % by weight |
|---|---|
| Irgasan DP 300 | 0.10 |
| n-Octyldodecanol | 0.50 |
| Microcapsules as described in Example 11 | 5.00 |
| Ethanol | 33.40 |
| Propane/butane 2:7 (propellant) | to 100.00 |

Example 26

Deodorant stick

| | % by weight |
|---|---|
| Irgasan DP 300 | 0.20 |
| Sodium stearate | 7.00 |
| 1,2-propylene glycol | 30.30 |
| Microcapsules as described in Example 11 | 20.00 |
| Triton X 100 | 4.00 |
| Ethanol | 31.00 |
| Fully-demineralized H₂O | 6,00 |

Example 27

Deodorizing spray pump action

| | % by weight |
|---|---|
| Irgasan DP 300 | 0.20 |
| Triton X 100 | 0.50 |
| Ethanol | 65.00 |
| Microcapsules as described in Example 13 | 12.00 |
| Perfume, colourants | q.s. |
| H₂O | to 100.00 |

Example 28

Deodorizing gel

| | % by weight |
|---|---|
| Chlorhexidine diacetate | 0.10 |
| Triton X 100 | 3.00 |
| Hydroxyethylcellulose | 0.50 |
| Ethanol | 40.00 |
| Microcapsules as described in Example 13 | 20.00 |
| perfume, colourants | q.s. |
| H₂O | to 100.00 |

Example 29

Deodorizing emulsion

| | % by weight |
|---|---|
| Irgasan DP 300 | 0.10 |
| Glyceryl stearate | 4.00 |
| PEG-40 cetylstearyl alcohol | 3.00 |
| 2-Octyldodecanol | 5.00 |
| Ethanol | 10.00 |
| Polyacrylate/methacrylate copolymer (Lubragel, Sederma) | 0.70 |
| Glycerol | 2.00 |
| Microcapsules as described in Example 13 | 15.00 |
| Perfume, colourants | q.s. |
| H₂O | to 100.00 |

We claim:

1. A method of effecting a cosmetic or pharmacological change in an individual which comprises topically applying to said individual a formulation containing a cosmetically or pharmacologically acceptable substance having a positive solution enthalpy, the substance being present in the formulation in an essentially anhydrous medium or being protected from an aqueous medium by means of a physical barrier.

2. Cosmetic and dermatological compositions containing one or more sugar alcohols of the general formula $$\begin{array}{c} CH_2OH \\ | \\ (CHOH)_n \\ | \\ CH_2OH \end{array}$$

where n=3, 4 and 5
and
where the sugar alcohol, or the sugar alcohols, are present in the formulations in an essentially anhydrous medium or are protected from an aqueous medium by means of a physical barrier.

3. Compositions according to claim 2, wherein the sugar alcohol is xylitol.

4. Compositions according to claim 2, wherein the substance, or the substances, which have a positive solution enthalpy, or the sugar alcohol, or the sugar alcohols, are in microencapsulated form.

5. Cooling cosmetic or medicinal topical formulations comprising xylitol which is present in the formulations in an essentially anhydrous medium or which is protected from an aqueous medium by means of a physical barrier.

6. Cosmetic or medicinal formulations according to claim 5, wherein in addition to xylitol, the formulations further contain at least one of the substances selected from the group comprising mannitol, sorbitol, propylene glycol, glycerol, urea, 2-pyrrolidone-5-carboxylic acid and its sodium salt, and sodium mannuronate.

7. Cosmetic and dermatological compositions according to claim 2, wherein they contain a combination consisting of
0.5–10.0 parts of xylitol
0.0–5.0 parts of mannitol
0.0–5.0 parts of sorbitol
0.0–5.0 parts of glycerol
0.0–5.0 parts of propylene glycol
0.0–5.0 parts of urea
0.0–5.0 parts of 2-pyrrolidone-5-carboxylic acid
0.0–5.0 parts of sodium 2-pyrrolidone-5-carboxylate
0.0–5.0 parts of sodium mannuronate,
based on the total composition, with the proviso that at least one of the non-xylitol components is at a concentration of at least 0.1% by weight.

8. Cosmetic and dermatological compositions according to claim 2, wherein at least one of the non-xylitol components is at a concentration of at least 1.0% by weight.

9. Formulations according to claim 5, wherein the xylitol is in microencapsulated form.

10. Formulations according to claim 6, wherein the formulations contain a composition consisting of
0.5–10.0 parts of xylitol
0.0–5.0 parts of mannitol
0.0–5.0 parts of sorbitol
0.0–5.0 parts of glycerol
0.0–5.0 parts of propylene glycol
0.0–5.0 parts of urea
0.0–5.0 parts of 2-pyrrolidone-5-carboxylic acid
0.0–5.0 parts of sodium 2-pyrrolidone-5-carboxylate
0.0–5.0 parts of sodium mannuronate,
based on the total composition of the formulation, with the proviso that at least one of the non-xylitol components is at a concentration of at least 0.1% by weight.

11. Formulations according to claim 10, wherein based on the total composition of the formulation, at least one of the non-xylitol components is at a concentration of at least 1.0% by weight.

* * * * *

UNITED STATES PATENT AND TRADEMARK OFFICE
CERTIFICATE OF CORRECTION

PATENT NO. : 5,861,440
DATED : January 19, 1999
INVENTOR(S) : Sven Gohla et al.

It is certified that error appears in the above-identified patent and that said Letters Patent is hereby corrected as shown below:

Col. 14, Line 2            Delete "2" and substitute --7--

Signed and Sealed this

Thirtieth Day of November, 1999

Attest:

Q. TODD DICKINSON

*Attesting Officer*     *Acting Commissioner of Patents and Trademarks*